US00PP17779P3

(12) United States Plant Patent
Lemon

(10) Patent No.: US PP17,779 P3
(45) Date of Patent: Jun. 5, 2007

(54) ***GERANIUM* PLANT NAMED 'ELEGANCE LAVENDER'**

(50) Latin Name: *Pelargonium×domesticum*
Varietal Denomination: Elegance Lavender

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 81 days.

(21) Appl. No.: 11/209,364

(22) Filed: Aug. 23, 2005

(65) Prior Publication Data

US 2006/0041980 P1 Feb. 23, 2006

Related U.S. Application Data

(60) Provisional application No. 60/603,817, filed on Aug. 23, 2004.

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent Bell
(74) *Attorney, Agent, or Firm*—The Webb Law Firm

(57) ABSTRACT

A new and distinct cultivar of Regal *Geranium* plant named 'Elegance Lavender', characterized by its early flowering; free-flowering habit; bright lavender-colored flowers with a purple eye and a mounded, bushy plant habit.

1 Drawing Sheet

Botanical classification: *Pelargonium×domesticum.*
Varietal denomination: 'Elegance Lavender'.

BACKGROUND OF THE INVENTION

The present invention comprises a new and distinct cultivar of *Pelargonium×domesticum* known by the varietal name 'Elegance Lavender'. The new variety was discovered in a selected breeding program in Lompoc, Calif. The new variety is a selection from the cross of unpatented proprietary breed variety Seedling #197 Lavender, as the female parent, and unpatented proprietary breed variety Seedling #102 Lavender, as the male parent. The new variety was first asexually reproduced by cuttings in Connellsville, Pa. The new variety has been trial and field tested and has been found to retain its distinctive characteristics and remain true to type through successive propagations.

The cultivar, when grown in a glass greenhouse in Connellsville, Pa. using natural light and temperatures of 60° F. night and 68° F. day, has a response time of twelve weeks from a rooted cutting to flowering in a 6 inch pot. The response time was determined on plants grown in soilless media employing constant fertilizer 150–200 parts per million of nitrogen and potassium in full light. The following traits have been repeatedly observed and are determined to be unique characteristics of 'Elegance Lavender'. Characteristics that distinguish 'Elegance Lavender' as a new and distinct cultivar from others known to the breeder include:

1. 'Elegance Lavender' is very early to flower;
2. Very free flowering;
3. Covers the plant very well with flowers; and
4. Earlier, with more free flowering than 'Emperor' (not patented).

DESCRIPTION OF THE DRAWING

The accompanying photographic drawing illustrates the new variety, with the color being as nearly true as is possible with color illustrations of this type.

DESCRIPTION OF THE PLANT

Figure 1:
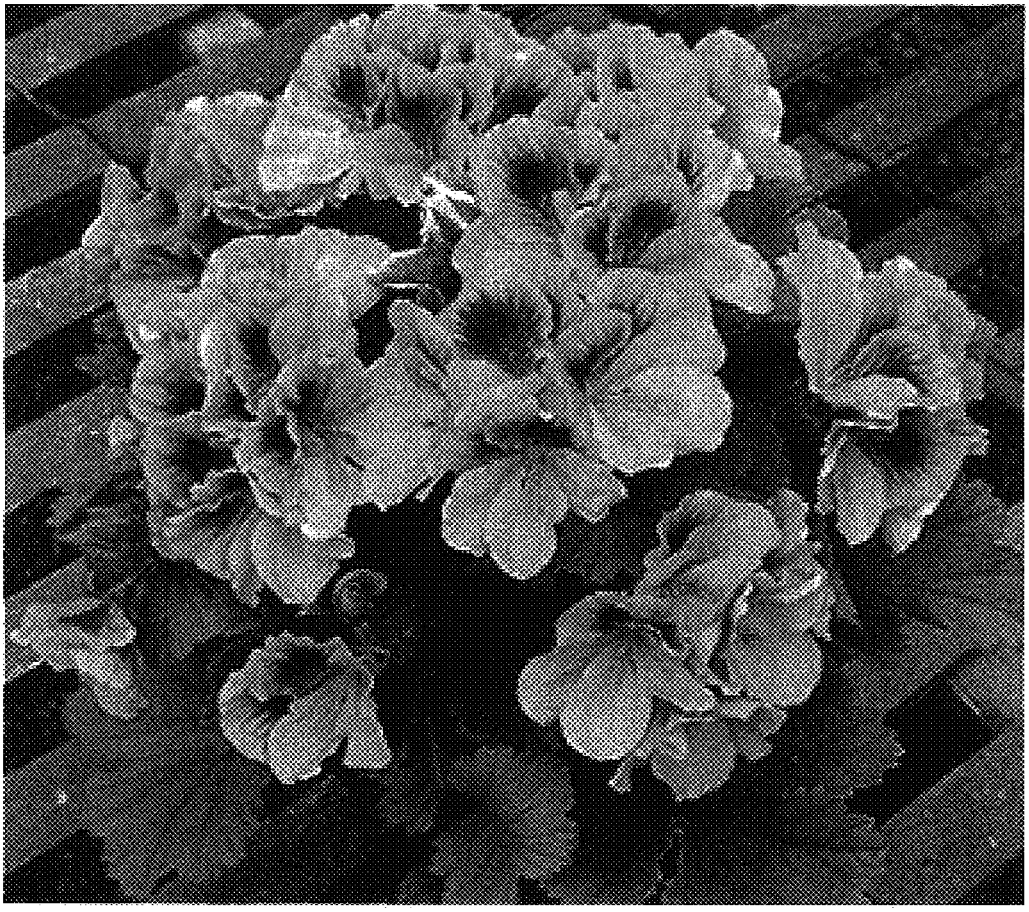

The following detailed description sets forth the characteristics of the new cultivar at fifteen weeks from potting a rooted cutting. The data which defines these characteristics were collected by asexual reproductions carried out by Oglevee, Ltd. in Connellsville, Pa. The color readings were taken on a plant under 65–85 foot candles of fluorescent cool white light. Color references are primarily to The R.H.S. Colour Chart of The Royal Horticultural Society of London.

PLANT

Form: Medium mound.
Height: 21–23 cm. from soil to top of foliage.
Growth: Upright, free basal branching.
Strength: Does not require artificial support.
Foliage: Stalked leaf attachment; medium green foliage.
Rooting time: Roots visible to outside of artificial medium plug in 25–28 days.
Leaves:
- *Arrangement.*—Alternate.
- *Stipules.*—Two per node.
- *Size.*—Length: 5–7 cm. Width: 6–8 cm.
- *Shape.*—Reniform; truncate base.
- *Margin.*—Serrated; lobed.
- *Texture.*—Leathery.
- *Pubescence.*—Pubescent.
- *Color.*—Upper surface: Green Group 137A. Lower surface: Green Group 138B.
- *Ribs and veins.*—Venation: Palmate. Color: Yellow-Green Group 146D.

Petioles:
- *Color.*—Yellow-Green Group 144A.
- *Length.*—2.9–3.8 cm.

Stem:
- *Color.*—Yellow-Green Group 144A.
- *Internode length.*—2.7–4.1 cm.

THE BUD

Development stage when bud characteristics were determined: Just prior to sepals parting at tips.

Shape of cluster:

*Overall.*—Elliptical cluster when no color showing.

*Individual bud.*—Elliptical or oval when no color showing.

Size:

*Overall.*—2.0–2.1 cm. across.

*Individual bud.*—1.3–1.7 cm. long; 0.7–0.9 cm. wide.

*Sepals.*—Five sepals; 1.4–1.5 cm. long; 0.4–0.5 cm. wide.

Number of buds per cluster: 4–9.

INFLORESCENCE

Blooming habit: Continuous; large florets forming full flower heads.

*Size* (*diameter of umbel*).—6.5–7.5 cm. across.

*Borne.*—Umbel; flower on pedicel; pedicel on peduncle 2–3 cm. above the foliage.

Florets:

*Form.*—Extremely cupped; cone shaped.

*Number of florets per umbel.*—4–9.

*Size.*—Diameter: 3.7–4.2 cm. across. Depth: 3.2–3.3 cm. deep.

*Sepals.*—Size: 1.7–1.8 cm. long; 0.3–0.6 cm. wide. Color: Green-Yellow Green Group 146D under and edges Greyed-Purple Group 187B.

*Petals.*—Upper petals have an eye (approximately the upper 3). Color: Upper surface: Upper petals: Outer edge is Purple Group 78B, some petals have a darker area near the outer edge of Purple Group 78A, moving to Purple Group 77C toward the outer edge near the base. The base of the petal is white. Some florets have petals of a brighter and darker tone at the outer edge being Red-Purple Group 74A, moving to Purple Group 77C. The eye color ranges from (nearest the outer edge of the petal): Red Purple Group 74B then Greyed-Purple Group 187A, after the darkest area, the eye fades Red-Purple Group 71A and Red-Purple Group 72A. Additionally, veining of Red-Purple Group 71A, Red-Purple Group 74A, and Greyed-Purple Group 187A is pronounced from the base extending through ¾ of the petal. Lower petals: Outer edge is Purple Group 78A, moving to Purple Group 75A near the center of the petal and fading to Purple Groups 75B and 75C near the base. Some petals are much brighter and darker than others being Red-Purple Group 74A at the outer edge moving to Red-Purple Group 71C. Some petals have streaks of Red-Purple Group 71D starting near the base of the petal extending through ¾ of the petal. Darker veining of Red-Purple Group 71A and Red-Purple Group 74A is present starting at the base and extending toward the outer edge through ¾ of the petal. Lower surface: Upper petals: Purple Group 78B, fading to Purple Group 78C, and Purple Group 78D near the base. Eye and veining show through. Lower petals: Purple Group 78C with streaks of Purple Group 78C fading to Purple Group 75D at the base.

*Shape.*—Inverted teardrop.

*Size.*—Length: 3.4–3.7 cm. Width: 2–2.9 cm. wide.

*Margin.*—Complete.

*Number per floret.*—5–9.

Texture and appearance: Smooth, velvety, highly reflective.

Tonality from a distance: Bright magenta-purple flowers with a striking royal purple-wine eye. Flowers saturate and nestle into a mound of bushy medium green foliage.

Petaloids:

*Quantity.*—None.

Pedicel:

*Length.*—1.5–1.6 cm.

*Color.*—Yellow-Green Group 145A at base moving to Green Group 137B near the calyx, some accent pigmentation of Greyed-Purple Group 187B.

Peduncle:

*Length.*—3.5–6.5 cm.

*Color.*—Yellow-Green Group 144A.

Disease resistance: No unusual susceptibility to diseases has been noted to date.

Pest resistance: No unusual susceptibility to pests has been noted to date.

Lasting quality: The individual umbels will last from 14–21 days. Overall blooming habit is continuous.

Fragrance: None.

REPRODUCTIVE ORGANS

Stamens:

*Quantity.*—0–2.

*Anthers.*—Length: 2–2.5 mm long; 0.5 mm thick. Color: White Group 155B to Red-Purple Group 73C.

*Filaments.*—Length: 7–9 mm. Color: White Group 155D. Pollen: Sparse.

Pistils:

*Number.*—One.

*Length.*—1.4–1.6 cm.

*Stigma.*—Number: One. Color: Deep orchid as it ages turning a muted purple-mauve.

*Style.*—Length: 0.8–0.9 cm. Color: Deep orchid.

Ovaries:

*Completeness.*—Superior.

*Pubescence.*—Highly pubescent.

*Length.*—7 mm.

*Width.*—3 mm.

*Color.*—Wine/burgundy (obscured by white pubescence).

Fruit: None observed.

I claim:

1. A new and distinct variety of *Geranium* plant named 'Elegance Lavender' as herein described and illustrated.

* * * * *

UNITED STATES PATENT AND TRADEMARK OFFICE

CERTIFICATE OF CORRECTION

PATENT NO. : PP 17,779 P3
APPLICATION NO. : 11/209364
DATED : June 5, 2007
INVENTOR(S) : Lemon It is certified that error appears in the above-identified patent and that said Letters Patent is hereby corrected as shown below:

On The Title Page Item (50) after line 2, "Varietal denomnination: "Elegance Lavender", insert the following:

-- CROSS-REFERENCE TO RELATED APPLICATION

This application claims the benefit of U.S. Provisional Plant Patent Application No. 60/603, 817 filed August 23, 2004, which is hereby incorporated by Reference in its entirety. --

Signed and Sealed this

Twentieth Day of November, 2007

JON W. DUDAS
*Director of the United States Patent and Trademark Office*